United States Patent [19]
Feinstein et al.

[11] 3,933,848
[45] Jan. 20, 1976

[54] PROCESS FOR THE PREPARATION OF PHENYLAMINES AND CARBAZOLES

[75] Inventors: Allen I. Feinstein, Wheaton; Ellis K. Fields, River Forest, both of Ill.

[73] Assignee: Standard Oil Company, Chicago, Ill.

[22] Filed: July 28, 1971

[21] Appl. No.: 167,021

[52] U.S. Cl............. 260/315; 260/465 E; 260/576; 260/578; 260/580; 260/612 R; 260/621 R; 260/645; 260/668 R; 260/689
[51] Int. Cl.² ....................................... C07D 209/86
[58] Field of Search.................. 260/580, 689, 315

[56] References Cited
OTHER PUBLICATIONS
C.A. 1: 682⁶, (1907), Lemoult.
Compt. Rend. 143: 772–775, (1906), Lemoult.
Ber. 35: 1606–1614, (1902), Bamberger.
J.A.C.S. 89: 3224–3228, (1967), Fields, et al.

*Primary Examiner*—Sherman D. Winters
*Attorney, Agent, or Firm*—James R. Henes; Arthur G. Gilkes; William T. McClain

[57] ABSTRACT

Nitrosobenzene or Azoxybenzene are heated at temperatures above about 400°C. to produce various phenylamines and carbazoles.

5 Claims, No Drawings

PROCESS FOR THE PREPARATION OF PHENYLAMINES AND CARBAZOLES

This invention relates to a method of thermally producing phenylamines. In one of its aspects, produced along with the principal products, phenylamines, such as aniline, diphenylamine etc., is a significant relative amount of phenylcarbazoles. The utility of various products of the present processes are well known. For example, diphenylamine has been variously employed in anti-oxidant additives and in stabilizers for plastics; carbazole is useful in the manufacture of dyes, explosives, rubber anti-oxidants and as a odor inhibitor in detergents.

According to the present invention a starting material of either nitrosobenzene or azoxybenzene is heated, in the presence of a suitable diluent, at a temperature above about 400°C. for a time sufficient for the synthesis of the desired phenylamines or carbazoles.

The nitrosobenzene and azoxybenzene starting materials are preferably unsubstituted; however, it is possible using the process of our invention to prepare substituted phenylamines and carbazoles by selecting substituted nitrosobenzenes and azoxybenzenes, as starting materials, wherein any or all of the rings in the starting material is substituted with halogen, cyano, alkyl groups up to $C_8$ and aryl.

The mechanism involved in the process of the present invention by which the phenylamines and carbazole products are produced is predominantly one of decomposition of the nitrosobenzene or azoxybenzene starting material. While the desired products could be prepared by subjecting solely the starting materials to the temperatures of the present invention, such a method—of necessity passing the starting materials through the melt phase poses certain problems. Since the reactions of the present invention proceed by free radical mechanism, the melt phase would create a reaction environment in which there was a high concentration of free radicals. Their interaction would result in the formation of tar-like, high molecular weight polyaryl compounds rather than the desired products. Thus the preferred way in which the process of the present invention is carried out is in the presence of a suitable diluent. Advantageously the starting material can be diluted with an inert gas. Examples of such a gas include nitrogen, helium and argon. The starting material in admixture with such an inert gas can then be brought to the temperature of the reaction zone. However, a more preferred class of diluents are solvents which are aromatic carbocyclic compounds having no aliphatic hydrogen. Exemplary of such solvents would be benzene, biphenyl, terphenyl etc. The selection of a liquid solvent permits a simple way of converting the starting materials into a form which can be conveniently introduced into and passed through the reaction zone. The molar ratio of the starting material to the diluent can range between 1:1 to about 1:20. The exact molar ratio is not critical and its selection is largely governed by solubility of the particular diluent for the starting material.

The process of the present invention may be carried out at a temperature between above about 400°C. up to about 850°C.; the preferred temperature range is 500°–600°C. As can be seen from Table I when the temperature drops below 400°C. the preferred products—phenylamines— are produced in progressively decreasing concentrations.

TABLE I

| Temperature Effects In Reaction of Nitrosobenzene In Benzene | | | | | |
|---|---|---|---|---|---|
| Temperatures,°C.: | 200 | 300 | 400 | 500 | 600 |
| Products | Relative Concentration | | | | |
| Nitrobenzene | 19.1 | 19.3 | 17.5 | 7.1 | 5.9 |
| Azoxybenzene | 76.1 | 75.7 | 62.1 | — | — |
| Azobenzene | 3.4 | 3.9 | 6.5 | — | — |
| Diphenylamine | Trace | 0.6 | 8.2 | 33.0 | 34.3 |
| Aminobiphenyls | — | — | — | — | 0.7 |
| Biphenyl | — | — | 2.7 | 37.4 | 30.2 |
| Phenol | 1.2 | 0.5 | 1.0 | 8.4 | 10.1 |
| Diphenyl Ether, Hydroxybiphenyls | — | — | — | — | 3.6 |
| Carbazole | — | — | 1.0 | 1.4 | 1.2 |
| Phenylcarbazoles | — | — | 1.0 | 11.5 | 12.0 |
| Triphenylamine | — | — | — | 1.0 | 1.4 |
| Aniline | — | — | — | Trace | 0.6 |

Above the aforesaid upper limit of temperature, the desired products have a tendency to decompose at rapid rates making recovery difficult. The residence time in the reaction zone may be varied between 1 second to 60 seconds; the preferred residence time being 10–20 seconds. Pressure is not critical to the process of the present invention; it being used merely as a convenience for controlling the gaseous reactants and their products. A pressure ranging between 1–10 atmospheres may be used advantageously; the preferred pressure being about 1 atmosphere.

In view of the relatively short residence times involved in the practice of our process, we have found it convenient to employ an inert gas to sweep the starting materials and products of the reactant through the reacting zone. Such inert gases as nitrogen, helium and argon are useful. However, such inert gases are not essential to the practice of this invention. For example, the vaporized solution of the starting material in a suitable solvent type diluent as aforementioned could be employed without the need for an additional inert gas carrier. For example, the nitrosobenzene could be dissolved in benzene, the solution then vaporized and introduced into the reaction zone; the continuous supply of vaporized solution being used to displace the reactor contents and provide fresh starting material to the reaction zone.

The following examples of the present invention are illustrative only and should in no way be construed as limiting the scope of the present invention as defined in the claims appended hereto.

EXAMPLE I

A solution of 0.1 mol of azoxybenzene in 0.5 mole of benzene were passed through a Vycor tube filled with Vycor chips at 600°C. under a helium flow of 20 cc/min. for a residence time of 16.1 seconds. The vapors from the reactor were condensed in a flask at 0°C.; the condensate was distilled giving 32.4 g. of benzene and 14.0 g. of product whose analysis is shown in Table II. Mass spectra for the analysis were measured in a modified Consolidated Model 21-103 instrument with the inlet system at 140°C.

EXAMPLE II

A solution of 0.1 mole of nitrosobenzene in 0.5 mole of benzene were reacted as in Example I except that the residence time was 9.5 seconds. The vapors were distilled and the analysis of the products was as shown in Table II.

TABLE II

| Products | Product Analysis Relative Concentrations | |
|---|---|---|
| | Nitrosobenzene | Azoxybenzene |
| Diphenylamine | 34.3 | 10.0 |
| Aminobiphenyls | 0.7 | 2.8 |
| Biphenyl | 30.2 | 33.8 |
| Diphenyl Ether, Hydroxybiphenyls | 3.6 | 2.4 |
| Phenol | 10.1 | 15.4 |
| Carbazole | 1.2 | 3.7 |
| Phenylcarbazoles | 12.0 | — |
| Azobenzene | — | 1.9 |
| Aniline | 0.6 | 30.0 |
| Nitrobenzene | 5.9 | — |
| Triphenylamine | 1.4 | — |

Thus, having described our invention, what we claim is:

1. A thermal process for the preparation of diphenylamines, phenyl carbazoles, and biphenyls as major products which comprises heating above about 400°C. a compound selected from the group consisting of nitrosobenzene and nitrosobenzene substituted with a material selected from the group consisting of halogen, cyano, aryl, and alkyl groups up to $C_8$ for a time sufficient to produce diphenylamines, phenyl carbazoles, and biphenyls.

2. The process of claim 1 wherein the compound, prior to heating, is mixed with a diluent which is an aromatic carbocyclic composition having no aliphatic-hydrogen in its structure, or which is a mixture of such compositions.

3. The process of claim 2 wherein the nitrosobenzene or nitrosobenzene substituted with a material selected from the group consisting of halogen, cyano, aryl, and alkyl groups up to $C_8$ is heated at a temperature between about 400°C. and about 850°C.

4. The process of claim 2 wherein the nitrosobenzene or nitrosobenzene substituted with a material selected from the group consisting of halogen, cyano, aryl, and alkyl groups up to $C_8$ is heated at a temperature between about 500°C. and about 600°C.

5. The process of claim 2 wherein the diluent is benzene.

* * * * *